(12) United States Patent
Uhlemann (10) Patent No.: US 9,511,242 B2
(45) Date of Patent: Dec. 6, 2016

(54) THERAPEUTIC APPARATUS COMPRISING A RADIOTHERAPY APPARATUS, A MECHANICAL POSITIONING SYSTEM, AND A MAGNETIC RESONANCE IMAGING SYSTEM

(75) Inventor: Falk Uhlemann, Hamburg (DE)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 77 days.

(21) Appl. No.: 13/992,793

(22) PCT Filed: Dec. 2, 2011

(86) PCT No.: PCT/IB2011/055432
§ 371 (c)(1),
(2), (4) Date: Jun. 10, 2013

(87) PCT Pub. No.: WO2012/080894
PCT Pub. Date: Jun. 21, 2012

(65) Prior Publication Data
US 2013/0261430 A1 Oct. 3, 2013

(30) Foreign Application Priority Data
Dec. 13, 2010 (EP) .................................... 10194683

(51) Int. Cl.
*A61B 5/05* (2006.01)
*A61N 5/10* (2006.01)
(Continued)

(52) U.S. Cl.
CPC ............. *A61N 5/1039* (2013.01); *A61B 5/055* (2013.01); *A61B 5/4836* (2013.01);
(Continued)

(58) Field of Classification Search
None
See application file for complete search history.

(56) References Cited

U.S. PATENT DOCUMENTS 2,730,566 A * 1/1956 MacLaughlin, Jr. et al. ............................ 378/98.6
5,945,684 A * 8/1999 Lam et al. ................. 250/492.3
(Continued)

FOREIGN PATENT DOCUMENTS

| CN | 1355055 A | 6/2002 |
| EP | 1121957 A2 | 8/2001 |

(Continued)

*Primary Examiner* — James Kish (57) ABSTRACT

A therapeutic apparatus (400, 500) comprising a radiotherapy apparatus (402), a mechanical positioning system, and a magnetic resonance imaging system (404). The radiotherapy apparatus comprises a radiotherapy source (408). The radiotherapy apparatus is adapted for rotating the radiotherapy source at least partially around a subject support. The therapeutic apparatus further comprises a memory containing machine executable instructions (468, 470, 472, 474, 476). Execution of the instructions causes a processor to repeatedly: acquire (100) the magnetic resonance data using the magnetic resonance imaging system; reconstruct (102) a magnetic resonance image (460) from the magnetic resonance data; register (104) a location (462) of the target zone in the magnetic resonance image; generate (106) radiotherapy control signals (464) in accordance with the location of the registered target zone; generate (108) mechanical positioning control signals (466) in accordance with the registered target zone and the radiotherapy control signals; and send (110) the radiotherapy control signals to the radiotherapy system and send (110) the mechanical positioning control signals to the mechanical positioning system.

13 Claims, 6 Drawing Sheets (51) Int. Cl.
*A61B 5/055* (2006.01)
*A61B 5/00* (2006.01)

(52) U.S. Cl.
CPC ......... *A61N 5/1067* (2013.01); *A61N 5/1077* (2013.01); *A61B 2090/374* (2016.02); *A61N 5/107* (2013.01); *A61N 2005/1055* (2013.01); *A61N 2005/1087* (2013.01); *A61N 2005/1095* (2013.01)

(56) References Cited

U.S. PATENT DOCUMENTS

| | | |
|---|---|---|
| 6,198,957 B1 | 3/2001 | Green |
| 7,473,913 B2 * | 1/2009 | Hermann et al. .......... 250/492.3 |
| 7,639,853 B2 | 12/2009 | Olivera |
| 2005/0197564 A1 * | 9/2005 | Dempsey ..................... 600/411 |
| 2008/0208036 A1 | 8/2008 | Amies |
| 2009/0149735 A1 | 6/2009 | Fallone |
| 2010/0113911 A1 | 5/2010 | Dempsey |
| 2011/0075815 A1 * | 3/2011 | Brown et al. ................. 378/125 |
| 2011/0156703 A1 * | 6/2011 | O'Connor .................... 324/307 |

FOREIGN PATENT DOCUMENTS

| | | |
|---|---|---|
| EP | 2196240 A1 | 6/2010 |
| WO | 9935966 A1 | 7/1999 |
| WO | 2004024235 A1 | 3/2004 |
| WO | 2007045075 A1 | 4/2007 |
| WO | 2010067227 A1 | 6/2010 |

* cited by examiner

THERAPEUTIC APPARATUS COMPRISING A RADIOTHERAPY APPARATUS, A MECHANICAL POSITIONING SYSTEM, AND A MAGNETIC RESONANCE IMAGING SYSTEM

CROSS-REFERENCE TO PRIOR APPLICATIONS

This application is the U.S. National Phase application under 35 U.S.C. §371 of International Application No. PCT/IB2011/055432, filed on Dec. 2, 2011, which claims the benefit of European Patent Application No.10194683.8, filed on Dec. 13, 2010. These applications are hereby incorporated by reference herein.

TECHNICAL FIELD

The invention relates to magnetic resonance guided radiotherapy, in particular to the control of a radiotherapy system and a mechanical positioning system in accordance with the magnetic resonance data.

BACKGROUND OF THE INVENTION

In routine practice of Radiotherapy (RT), the subject is positioned relative to the stationary center of the rotating arc carrying the RT source. Positioning implies both height and lateral adjustment of the subject table. This positioning is required to optimize the dose in the lesion beyond variation that can be obtained by applying RT rays from different angles.

Integration of MR and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (CTV) from multiple angles while minimizing the radiation exposure for surrounding tissues.

The combination of magnetic resonance apparatuses and LINAC radiotherapy sources is known. Typically a LINAC source is placed on a rotating gantry about the magnet and the magnet designed such that the LINAC rotates in a zero-field region of the magnet. Another particular feature of the concept is the use of a split gradient coil which prevents attenuation of the LINAC beam.

United States patent application US 2009/0149735 discloses a combined radiation therapy system and magnetic resonance imaging apparatus. An interface which acts between the radiation source and the MRI apparatus permits irradiation to be performed simultaneously with imaging.

SUMMARY OF THE INVENTION

The invention provides for a therapeutic apparatus, a computer program product, and a method of controlling a therapeutic apparatus in the independent claims. Embodiments are given in the dependent claims.

Current radiation therapy systems typically use multileaf collimators (MLC) for precise adjustment of radiation sources. The MLC consists of numerous thin metal plates which are controlled and moved by mechanical drives to shape the radiation beam. It is one of the most critical (design complexity, material and manufacturing cost, control failures, radiation leakage, reliability issues . . . ) components of a radiation therapy device.

Novel integrated magnetic resonance image (MRI) guided RT devices allow high resolution real-time imaging of the target region during irradiation. However, multileaf collimators may be expensive. Embodiments of the invention may eliminate the need for a multileaf collimator or allow the use of a simpler and less expensive multileaf collimator by performing Magnetic Resonance Imaging (MRI) tracking a real-time control-loop for steering and modulating the radiation beam of constant size. This may have the benefit of reducing device complexity and/or cost and/or size significantly. Reliability and radiation leakage issues could be resolved and treatment precision increased via real-time beam modulation.

Some embodiments use a cylindrical collimator with multiple pencil beam collimators. The cylindrical collimator can be described as a "revolver collimator."

Radiation therapy (RT) is one of the most effective options for tumor treatment (others are surgery, chemotherapy). During the RT procedure a radiation source (e.g. linear accelerator—LINAC/magnetron) produces high energy radiation (e.g. photons) which is able to break the DNA of cells thereby killing them. Because it destroys malignant as well as healthy cells alike it has to be focused on the well-defined target region via spatial/temporal/intensity modulation. Currently this is achieved with components like secondary collimators, diaphragms and multileaf collimators (MLC). The MLC consists of stepped metal plates (leaves) which are positioned in the radiation path as absorbers and can be controlled and moved very precisely by micro-motors. This allows shaping the beam and adapting it to the projection of the target region (tumor shape) which is called three-dimensional conformal radiotherapy. Real-time imaging (e.g. integrated secondary X-ray imaging, use of RT-radiation transmission, MR) during RT allows to adjust the treatment beam during the procedure resulting in image-guided RT (IGRT).

Different designs of MLCs are currently in use but they may have the following limitations in common:
  Leaf width at centre (>1.5 mm) results in a limited spatial resolution orthogonal to leaf plane surface
  Number of leaf pairs (~20 . . . 120) results in a high number of mechanical drives and (optical) sensors results in high complexity and relatively low reliability
  Maximum field size (~40 cm×40 cm) results in a limited treatment area (without repositioning of patient)
  Leaf movement speed limits the speed of beam shape adaptation
  Interleaf radiation leakage (2 . . . 5%) results in a necessity of backup collimator to reduce leakage
  To enable image guided radiotherapy, the high requirements regarding accuracy and/or repeatability and/or speed and/or control of leaf positioning, shielding, compactness, mechanical load and patient safety lead to a complex/expensive and unfortunately failure prone MLC component.

Embodiments of the invention may perform real-time imaging (e.g. MRI) in conjunction with patient table and (e.g. pencil shaped) beam control allows tracking of target regions (tumors) and simultaneous beam steering and/or switching in conjunction with patient positioning to direct the radiation at the target. This allows to eliminate the need for complex, expensive and failure prone beam shaping (e.g. with MLCs).

Some embodiments of the invention are significantly simplified compared to the current systems in use because the multileaf collimator and the diaphragms (used to reduce leaf radiation leakage) are substituted by a simple collimating block (e.g. pencil beam collimator).

In some embodiments, a simple pencil beam collimator may have a smaller maximum opening than a MLC which results in a smaller irradiated area (lower dose, longer treatment time). However, this could be compensated by the faster operation of the significantly simplified gantry or a cylindrical collimator with multiple pencil beam collimators. Such a collimator could be rotated in discrete angular steps to bringing the desired collimator section in the radiation path thereby creating radiation beams of different diameters without the numerous problems previously listed for MLCs.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' as used herein encompasses to any device comprising a processor. A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, parallel port, IEEE 1284, serial port, RS-232 port, IEEE-488 port, Bluetooth connection, Wireless local area network connection, TCP/IP connection, Ethernet connection, control voltage interface, MIDI interface, analog input interface, and digital input interface.

'Medical image data' as used herein encompasses two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

'Magnetic Resonance (MR) data' as used defined herein encompasses the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a therapeutic apparatus comprising a radiotherapy apparatus for treating a target zone of a subject. The radiotherapy apparatus comprises a radiotherapy source for directing electromagnetic radiation into the target zone. The electromagnetic radiation may be high energy photons generated for example, but not limited to: an x-ray source, a LINAC x-ray source, and a radioisotope gamma radiation source. A radioisotope gamma radiation source as used herein encompasses a radiation source for generating gamma radiation that uses a radioisotope.

In some embodiments the radiotherapy apparatus may comprise a gantry for moving the radiotherapy source. The therapeutic apparatus further comprises a mechanical positioning system for positioning a subject support. The mechanical positioning system is able to physically move the subject support. The therapeutic apparatus further comprises a magnetic resonance imaging system for acquiring magnetic resonance data from an imaging zone. The target zone is within the imaging zone. The magnetic resonance imaging system comprises a magnet for generating a magnetic field within the imaging zone. The radiotherapy apparatus is adapted for rotating the radiotherapy source at least partially around the subject support. In some embodiments the radiotherapy source in its entirety is rotated. In other embodiments only a portion of the radiotherapy source is rotated. In some embodiments the magnet and the subject support are rotated at the same time. The magnet may have a hole or path which allows the radiotherapy source to irradiate the subject. In some embodiments the radiotherapy apparatus is adapted for rotating the radiotherapy source at least partially around the magnet.

The therapeutic apparatus further comprises a processor for controlling the therapeutic apparatus. As used herein a processor may also be multiple processors. For instance a single computer system may have more than one processor. Also references to a processor may also refer to processors distributed in multiple computer systems.

The therapeutic apparatus further comprises a memory containing machine executable instructions for execution by the processor. Execution of the instructions causes the processor to repeatedly acquire the magnetic resonance data using the magnetic resonance imaging system. After acquiring magnetic resonance data execution of the instructions cause the processor to repeatedly reconstruct a magnetic resonance image from the magnetic resonance data. Execution of the instructions further causes the processor to register a location of the target zone in the magnetic resonance image. This may be achieved using standard registration techniques. For instance models of the anatomy that was imaged may be used or trained or self-loading models may also be used.

Execution of the instructions further cause the processor to generate radiotherapy control signals in accordance with the location of the registered target zone. The radiotherapy control signals cause the radiotherapy source to irradiate the target zone. The radiotherapy control signals are control signals which may be used to control the duration, intensity, energy and location of the radiotherapy source. Execution of the instructions further causes the processor to generate mechanical positioning control signals in accordance with the registered target zone and the radiotherapy control signals. The mechanical positioning control signals cause the mechanical positioning system to position the subject. Essentially on the basis of the registered magnetic resonance image both the radiotherapy control signals and the mechanical positioning control signals are generated.

Execution of the instructions further causes the processor to send the radiotherapy control signals to the radiotherapy system and send the mechanical positioning control signals to the mechanical positioning system. At this point if the therapy is finished the instructions would cause the processor to stop irradiating the target zone. However if the therapy is still continuing the instructions will cause this process to loop and the processor will acquire the magnetic resonance data using the magnetic resonance imaging system and repeat the process that was just described. Embodiments of this method are particularly advantageous because magnetic resonance data is acquired repeatedly and this is used to send radiotherapy control signals and mechanical positioning control signals to modify the treatment of the target zone.

In another embodiment the radiotherapy source comprises a pencil-beam collimator. A pencil-beam collimator as used herein encompasses a collimator which has a fixed aperture. A pencil-beam collimator is intended to collimate a radiation beam or beam of electromagnetic radiation into a clearly defined radiation beam.

In another embodiment the radiotherapy source comprises a cylindrical collimator assembly. The cylindrical collimator assembly comprises multiple pencil-beam collimators including the pencil-beam collimator. The cylindrical-shaped collimator assembly has a rotational axis. The radiation source has a beam path. Rotation of the cylindrical-shaped collimator assembly causes a selected beam collimator chosen from the multiple pencil-beam collimators to rotate into the beam path. The cylindrical collimator assembly may have an axis of rotation. Rotation about this axis may cause different pencil-beam collimators to be rotated into the beam path. This has several benefits. The first benefit is this allows different pencil-beam collimators to be selected. Also rotating the cylindrical collimator assembly about its axis allows the position of the collimator to be changed slightly. In some embodiments rotation of the collimator assembly is used simply for selecting different collimators. In other embodiments rotation of the assembly by a small amount may simply cause the beam path of the radiation source to shift slightly.

In another embodiment the radiotherapy control signals comprise commands which cause the cylindrical collimator assembly to select the selected beam collimator. Essentially the radiotherapy control signals are sent to the radiotherapy system and this causes the cylindrical collimator to move or rotate a particular pencil-beam collimator into the beam path. This is advantageous because pencil-beam collimators of different sizes can be selected. This may assist in optimally treating the target zone of the subject.

In another embodiment the radiotherapy control signals comprise commands which cause controlled angular rotation of the cylindrical assembly as a function of time. This is advantageous because controlled rotation of the cylindrical assembly may allow the beam path to be shifted slightly.

In another embodiment the radiotherapy source is mounted on a gantry which rotates about a rotational axis. In some embodiments the radiotherapy source is mounted such that it is directed towards an axis of rotation.

In another embodiment the radiotherapy apparatus is adapted for tilting the radiotherapy source and/or the collimator. An adjustable collimator could be tilted, a pencil-beam collimator could be tilted, and a cylindrical collimator could be tilted with respect to an axis of rotation of the radiotherapy source.

In another embodiment the directing of the electromagnetic radiation into the target zone is at least partially controlled by the angular rotation of the cylindrical assembly as a function of time.

In another embodiment the radiotherapy control signals comprise commands which cause the radiotherapy system to perform any one of the following as a function of time: adjust the timing of the radiation source, adjust the intensity of the radiation source, control the angular position of the radiation source relative to the magnet, and combinations thereof. By adjusting the timing of the radiation source this may be interpreted as turning the radiation source on or off. For some embodiments such as an X-ray source or a Linac the intensity of the radiation source can be adjusted. The radiotherapy apparatus is adapted for rotating at least partially around the subject support. Rotational control of the radiotherapy source about or around the subject support is equivalent with controlling the angular position of the radiation source relative to the target zone of the subject.

This embodiment is advantageous because the direction of radiation into the target zone can be precisely controlled.

In another embodiment the mechanical positioning control signals cause the mechanical positioning system to adjust the position of the subject support as a function of time. This embodiment is advantageous because the adjustment of the position of the subject support allows the movement of a subject relative to the radiotherapy source. This may allow for the compensation of external and/or internal motion of a subject during the process of treating the target zone.

In another embodiment the location of the target zone is co-registered to the subject support, the radiotherapy apparatus, and the magnetic resonance imaging system. This embodiment is particularly advantageous because the coordinate systems of the subject support, the radiotherapy apparatus, and the magnetic resonance imaging system are correlated. That is to say if the coordinates are of an object or a location or known in one of the three then it is also known in the others. This is advantageous because images or magnetic resonance data taken using the magnetic resonance imaging system can be used to determine the location of the target zone relative to the coordinate systems of the subject support and the radiotherapy apparatus. This enables the control of the subject support and the radiotherapy apparatus to accurately direct radiation into the target zone.

In another embodiment the radiotherapy source comprises an adjustable beam collimator. The updated radiotherapy control signals comprise commands for controlling the beam collimator. The radiotherapy control signals may comprise commands for controlling the beam collimator as a function of time. This may be used for at least partially compensating for motion of the subject either externally or internally. The adjustable beam collimator may be for instance a multi-leaf collimator. An adjustable beam collimator as used herein encompasses a collimator for a radiation beam or source which is able to change its aperture or profile as a function of time. Multi-leaf collimators function by moving a collection of plates to adjust the shape and/or size of the aperture.

In another embodiment the repeated execution of the machine executable instructions forms a closed controller for directing electromagnetic radiation into the target zone. The magnetic resonance data is repeatedly acquired and the magnetic resonance data is used to generate updated radiotherapy control signals and mechanical positioning control signals. This forms a closed control loop.

In another embodiment the radiotherapy source is a LINAC X-ray source or linear accelerator X-ray source.

In another embodiment the radiotherapy source is a LINAC for generating x-ray or gamma radiation. The magnet is adapted for generating a low magnetic field zone which encircles the magnet. The radiotherapy apparatus is adapted such that the radiotherapy source rotates about the magnet within the low magnetic field zone. The magnetic field strength within the low magnetic field zone is below an operational threshold of the LINAC source. The operational threshold defines a magnetic field strength which prevents the LINAC source from functioning properly. In modern cylindrical bore magnetic resonance imaging magnets there are typically several compensation coils. The compensation coils generate a magnetic field which is opposed to coils used to generate the main magnetic field. This results in an area outside of the cylindrical magnet approximately in the mid-plane which is doughnut-shaped and has a low magnetic field. The low magnetic field zone may be this doughnut-shaped zone surrounding the cylindrical magnet with compensation coils.

In another embodiment the operational threshold is below 5 mT, preferably below 10 mT.

In another embodiment the radiotherapy source is an X-ray tube. When the radiotherapy source is an X-ray tube, it is advantageous to either place the X-ray tube within the bore of the magnet or use a split magnet. A split magnet uses two cylindrical magnet sections as a single magnet. Typically split magnets have a open area at the isoplane which allows direct access to the subject.

In another embodiment the radiotherapy source is a radioisotope gamma radiation source. A radioisotope gamma radiation source as used herein encompasses a radiation source which uses a radioisotope to generate gamma radiation.

In another embodiment the radiotherapy source is a carbon nanotube X-ray source. When the radiotherapy source is an nanotube X-ray source, it is advantageous to either place the X-ray tube within the bore of the magnet or use a split magnet. A split magnet uses two cylindrical magnet sections as a single magnet. Typically split magnets have a open area at the isoplane which allows direct access to the subject.

In another embodiment the radiotherapy source is a proton beam source. For a proton beam source it may be advantageous to use a so-called split magnet so that the proton beam has access to the target zone of the subject.

In another embodiment the radiotherapy source is a charged particle beam source. For the case where the radiotherapy source is a charged particle beam source it is also advantageous to use a so-called split magnet.

In another embodiment the radiotherapy source is a neutron beam source. For a neutron beam source it may also be advantageous to use a split magnet.

In another embodiment the radiotherapy source is a carbon ion source. The carbon ion source also uses charged particles. In this embodiment it is also advantageous to use a so-called split magnet.

In another aspect the invention provides for a computer program product comprising machine executable instructions for execution by a processor for controlling a therapeutic apparatus. The computer program product or program may for instance be sorted on a computer-readable storage medium. The therapeutic apparatus comprises a radiotherapy apparatus for treating a target zone of a subject. The radiotherapy apparatus comprises a radiotherapy source for directing electromagnetic radiation into the target zone. The therapeutic apparatus further comprises a mechanical positioning system for positioning a subject support. The therapeutic apparatus further comprises a magnetic resonance imaging system for acquiring magnetic resonance imaging data from an imaging zone. The target zone is within the imaging zone.

The magnetic resonance imaging system comprises a magnet for generating a magnetic field within the imaging zone. The radiotherapy apparatus is adapted for rotating the radiotherapy source at least partially around the subject support. Execution of the instructions causes the processor to repeatedly acquire the magnetic resonance data using the magnetic resonance imaging system. After acquiring magnetic resonance data execution of the instructions further causes the processor to reconstruct a magnetic resonance image from the magnetic resonance data. After reconstructing the magnetic resonance image execution of the instructions further cause the processor to register a location of the target zone in the magnetic resonance image.

Execution of the instructions further cause the processor to generate radiotherapy control signals in accordance with the location of the registered target zone. The radiotherapy control signals cause the radiotherapy source to irradiate the target zone. Execution of the instructions further causes the processor to generate mechanical positioning control signals in accordance with the registered target zone and the radiotherapy control signals. The mechanical positioning control signals cause the mechanical positioning system to position the subject. Execution of the instructions further causes the processor to send the radiotherapy control signals to the radiotherapy system and send the mechanical position control signals to the mechanical positioning system.

In another aspect the invention provides for a method of controlling a therapeutic apparatus. The method may also be implemented by a computer and therefore the invention also provides for a computer-implemented method of controlling the therapeutic apparatus. The therapeutic apparatus comprises a radiotherapy apparatus for treating a target zone of a subject. The radiotherapy apparatus comprises a radiotherapy source for directing electromagnetic radiation into the target zone. The therapeutic apparatus further comprises a mechanical positioning system for positioning a subject support. The therapeutic apparatus further comprises a magnetic resonance imaging system for acquiring magnetic resonance imaging data from an imaging zone. The target zone is within the imaging zone. The magnetic resonance imaging system comprises a magnet for generating a magnetic field within the imaging zone.

The radiotherapy apparatus is adapted for rotating the radiotherapy source at least partially around the subject support. The method comprises repeatedly performing the step of acquiring the magnetic resonance data using the magnetic resonance imaging system. After the magnetic resonance data has been acquired the following steps are repeated after acquiring the magnetic resonance data. The method further comprises the step of reconstructing the magnetic resonance image from the magnetic resonance data. The method further comprises the step of registering a location of the target zone in the magnetic resonance image. The method further comprises the step of generating radiotherapy control signals in accordance with the location of the registered target zone. The radiotherapy control signals cause the radiotherapy source to irradiate the target zone. In an alternative embodiment, the magnet of the magnetic resonance imaging system and the radiotherapy device are connected and rotate together. The magnet has a clearance hole or path which allows the radiotherapy source to irradiate the subject. In some embodiments, the radiotherapy apparatus is adapted for rotating the radiotherapy source at least partially around the subject support.

The method further comprises the step of generating mechanical positioning control signals in accordance with the registered target zone and the radiotherapy control signals. The mechanical positioning control signals cause the mechanical positioning system to position the subject. The method further comprises the step of sending the radiotherapy control signals to the radiotherapy system and sending the mechanical positioning control signals to the mechanical positioning system. These steps may be repeated in sequence until the treatment of the target zone is complete.

According to an aspect of the invention, the radiotherapy apparatus comprises a switchable radiotherapy source to generate therapeutic radiation and a collimator assembly to form a pencil beam from the therapeutic radiation, the collimator assembly including an aperture block having a radiation transparent window a rotatable collimator member with several channels the aperture block being positioned between the radiotherapy source and the rotatable collimator member and a control unit is provided to switch the radiotherapy source on/off on the basis of the angular position of the collimator member.

The aperture block forms a collimated radiation beam from the radiation generated by the radiotherapy source. The transverse diameter of the collimated beam corresponds to the diameter of the radiation transparent window. The collimated beam impinges on the rotatable collimator member. When a channel of the rotatable collimator is at the transparent window, the pencil beam is formed from the collimated beam. The transverse diameter of the pencil beam corresponds to the width of the channel along the beam path of the collimated beam. As the rotatable collimator member is rotated around its axis of rotation, the several channels are moved with respect to the transparent window of the aperture block. When, under the control of the control unit, the radiotherapy source is switched on when one of the channels is at the transparent window, the pencil beam is formed by that channel. As the collimator member rotates, different channels are moved in succession in position at the transparent window. By switching the radiotherapy source on or off as the channels are positioned at the transparent window, one may select the channel by which the pencil beam is formed. Because the individual channels are located at different positions in the collimator member, selection of the channel to form the pencil beam causes the pencil beam to be directed at different locations in the object to be irradiated. Thus, the collimator assembly with the control of the switching of the radiotherapy beam enables spatial control of the therapeutic radiation disposed in the object. The collimator assembly of the present invention has simpler components and is less expensive to manufacture than a conventional multi-leaf collimator.

In a preferred embodiment the rotatable collimator member is a rotatable disk in which said channels are provided at different radial positions and azimuthal orientations relative to the disk's centre of rotation. As the rotatable disk is rotated, each of the channels in succession forms a pencil beam having their beam paths at a different spatial locations. These various beam paths impinge at different positions on the object to be orientated. These positions on the object can actually be irradiated by switching on the radiotherapy source at the moment when the channel at issue is placed at the transparent window of the aperture block. Variations of this configuration include groups of channels with different diameters within the rotatable disk for different pencil beam diameters, filling of the channels with different (weakly) radiation absorbing media for intensity modulation or a spiral notch (instead of discrete holes in the rotating disk) for a continuous radial movement of the emerging pencil beam location.

Thus the collimator assembly with the control of the radiotherapy source allows to accurately control the region of the object that is actually irradiated. Notably, regions with sensitive tissue that is to be preserved is accurately shielded from the therapeutic radiation. The different positions that are irradiated by the various channels can be used to build-up radiation dose when these positions are repeatedly irradiated as the rotatable disk rotates. This enables to accurately irradiate a region that has a complicated geometrical shape. Notably according to this aspect of the invention, such a complicated geometrical shaped region can be accurately irradiated with the use of simple and cheap mechanical components.

The collimator assembly of this aspect of the invention is able to form the pencil beam from therapeutic electromagnetic radiation such as hard x-radiation or γ-radiation. Also pencil beams of particle radiation such as protons or neutrons can be formed by the collimator assembly of the invention.

It is also noted that this aspect of the invention can be employed independently of the image guiding of the pencil beam on the basis of the target zone being registered from an magnetic resonance image. That is, in the present aspect of the invention, the pencil beam can be controlled on the basis of a radiotherapy plan that is available in the controller of the collimator assembly and the radiotherapy source. This radiotherapy plan can be set up on the basis of pre-recorded diagnostic images. As an option, the radiotherapy plan can be updated during the irradiations by the pencil beam on the basis of magnetic resonance images that are made during carrying-out the radiotherapy plan, e.g. to update the location of the target zone.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
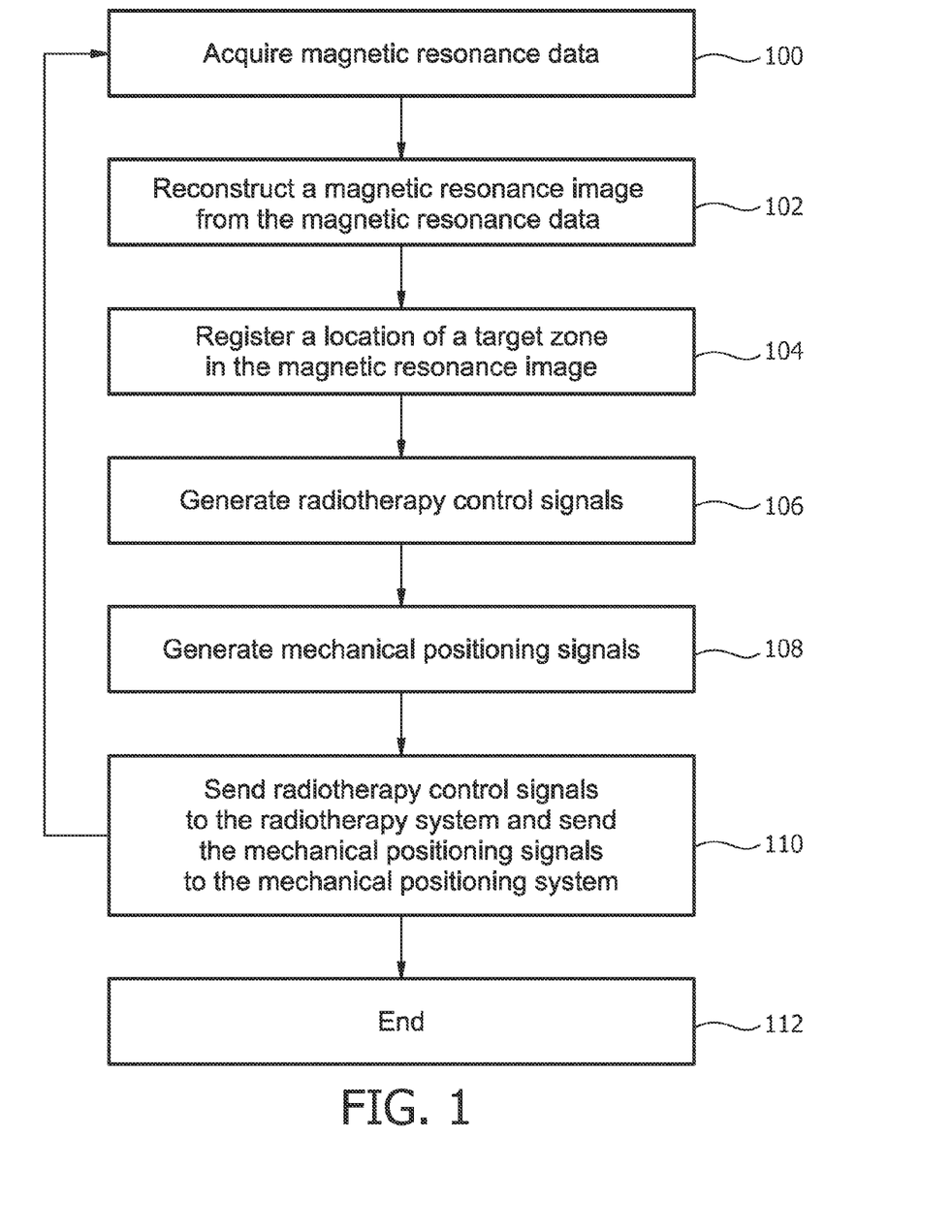
FIG. 1 shows a flow diagram which illustrates an embodiment of a method according to the invention.

FIG. 1 shows a flow diagram which illustrates an embodiment of a method according to the invention. The method may also be implemented or performed as a computer-implemented method or as a computer program product in the form of machine executable instructions.

In step 100 magnetic resonance data is acquired. In step 102 a magnetic resonance image is reconstructed from the magnetic resonance data. Typically magnetic resonance data is acquired for a volume or a thin volume referred to as a slice. References to a magnetic resonance image may also refer to multiple images or multiple slices. Next in step 104 a location of the target zone is registered in the magnetic resonance image. This may be performed using standard image registration techniques. For instance a model of the specific anatomy may be used to identify anatomical landmarks which are then used to locate the target zone. Next in step 106 radiotherapy control signals are generated using the registration on the magnetic resonance image.

Next in step 108 mechanical positioning signals are also generated from the magnetic resonance image. The control of the radiotherapy system and also the mechanical positioning system both effect which region of the subject will be targeted. Therefore the radiotherapy control signals and the mechanical positioning signals are generated complimentary, that is to say they are generated in conjunction with each other. Next in step 110 radiotherapy control signals are sent to the radiotherapy system and the mechanical positioning signals are sent to the mechanical positioning system. If therapy of the target zone is continuing then the method repeats back to step 100 and more magnetic resonance data is acquired. If the therapy is finished then the method ends at step 112.

Figure 2:
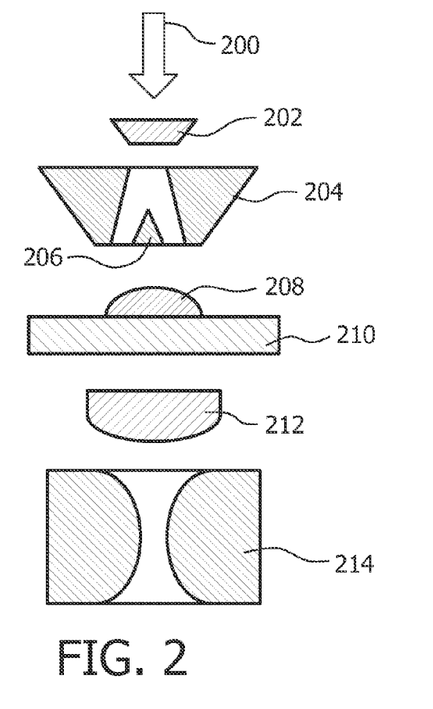
FIG. 2 illustrates an embodiment of a radiation source according to the invention.

FIG. 2 illustrates an embodiment of a radiation source according to the invention. The arrow labeled 200 represents a radiation beam for instance a beam of electrons which have been accelerated by an accelerator. The radiation beam then strikes target 202. This generates high energy X-rays or gamma radiation. After being generated the radiation then travels through a primary collimator 204. The primary collimator 204 performs a preliminary beam shaping. The primary collimator 204 comprises a beam homogenizer 206. This cone-like region performs the homogenizing of the beam. Next the beam goes through a flattening filter 208. The flattening filter helps to make the beam more uniform and homogeneous. Next the beam travels through an ion chamber 210 to measure the dose of the radiation. If the dose is too high the amount of electrons in the radiation beam 200 can be reduced. Next after going through the ion chamber 210 the radiation beam passes through a wedge 212 which functions to further flatten or homogenize the beam. Finally the beam passes through a pencil collimator 214. The pencil collimator is used to collimate the beam into a narrow beam. In other embodiments the pencil collimator 214 could be replaced with a multi-leaf collimator. Within the framework of the present invention the radio therapy source may be any one of the following: LINAC X-ray source, and X-ray tube, a radio isotope gamma radiation source, a carbon nanotube X-ray source, a proton beam source, charged particle beam source, a neutron beam source, and a carbon ion source.

Figure 3:
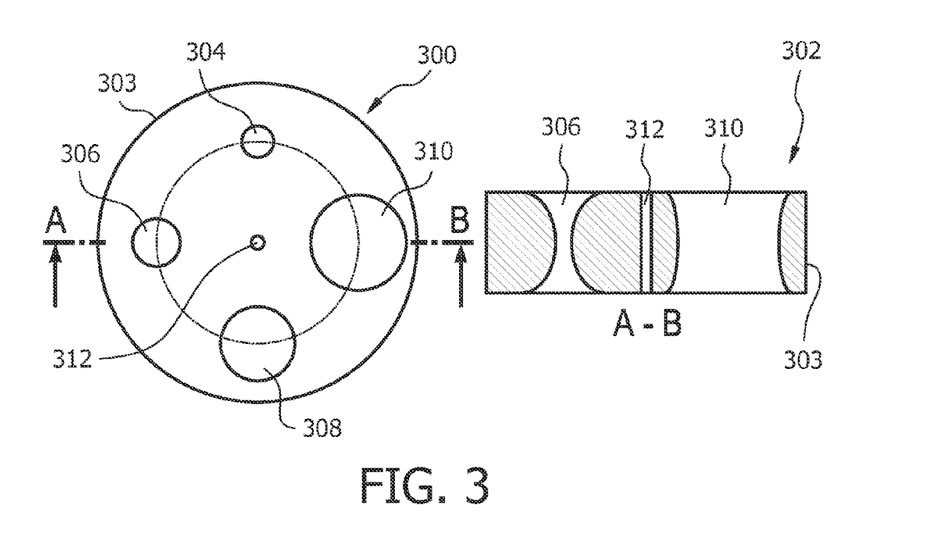
FIG. 3 shows a top view and a cross-sectional view of a cylindrical collimator assembly.

FIG. 3 shows a top view 300 and a cross-sectional view 302 of a cylindrical collimator assembly 303. The cylindrical collimator assembly is cylinder-shaped. On the top view there are visible a first collimator 304, a second collimator 306, a third collimator 308, and a fourth collimator 310. There is a bearing hole 312 about which the cylindrical collimator assembly can rotate. The cross-sectional view is performed across the dashed line labeled AB. In the cross-sectional view 302 the second collimator 306, the fourth collimator 310 and the bearing hold 312 are visible.

Figure 4:
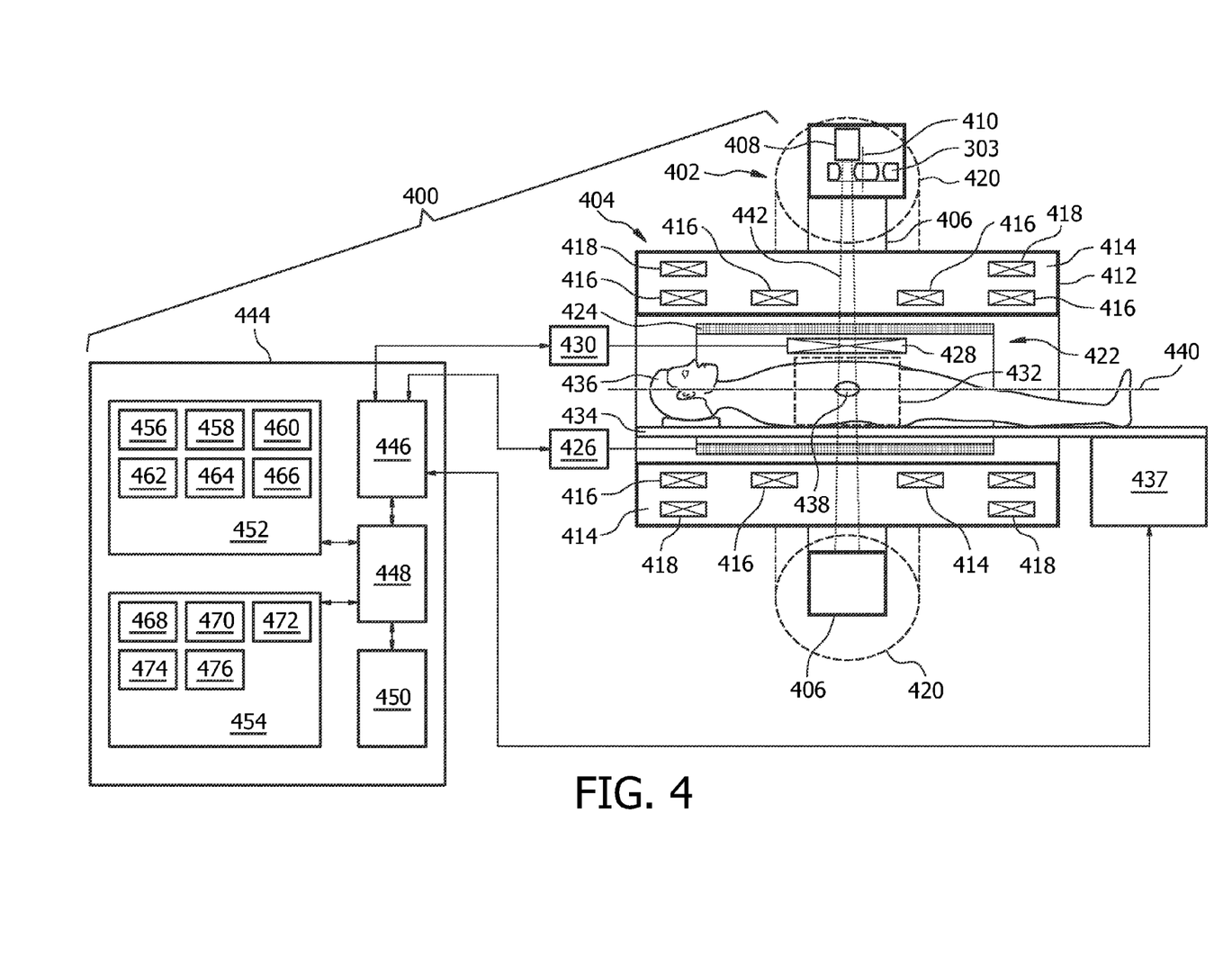
FIG. 4 shows an embodiment of a therapeutic apparatus according to the invention.

FIG. 4 shows an embodiment of a therapeutic apparatus 400 according to the invention. The therapeutic apparatus 400 comprises a radiotherapy apparatus 402 and a magnetic resonance imaging system 404. The radiotherapy apparatus 402 comprises a gantry 406 and a radiotherapy source 408. The gantry 406 is for rotating the radiotherapy source 408 about an axis of gantry rotation 440. Adjacent to the radiotherapy source 408 is a cylindrical collimator assembly 303. The cylindrical collimator assembly has a rotational axis 410 for rotating different pencil collimators in front of the radiotherapy source 408. The magnetic resonance imaging system 404 comprises a magnet 412.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

The magnet 412 shown in this embodiment is a standard cylindrical superconducting magnet. The magnet 412 has a cryostat 414 with superconducting coils within it 416. There are also superconducting shield coils 418 within the cryostat also. The superconducting shield coils 418 cause a low magnetic field region 420. The low magnetic field region 420 encircles the magnet 412. The magnet 412 has a bore 422.

Within the bore of the magnet is a magnetic field gradient coil 424 for acquisition of magnetic resonance data to spatially encode magnetic spins within an imaging zone of the magnet. The magnetic field gradient coil 424 is connected to a magnetic field gradient coil power supply 426. The magnetic field gradient coil 424 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 426 supplies current to the magnetic field gradient coils. The current supplied to the magnetic field coils is controlled as a function of time and may be ramped or pulsed.

There is a radio frequency coil 428 connected to a transceiver 430. The radio frequency coil 428 is adjacent to an imaging zone 432 of the magnet 412. The imaging zone 432 has a region of high magnetic field and homogeneity which is sufficient for performing magnetic resonance imaging. The radio frequency coil 428 may is for manipulating the orientations of magnetic spins within the imaging zone and for receiving radio transmissions from spins also within the imaging zone. The radio frequency coil 428 may also be referred to as an antenna or channel. The radio frequency coil 428 may contain multiple coil elements. The radio frequency antenna may also be referred to as a channel.

The radio frequency coil 428 and radio frequency transceiver 430 may be replaced by separate transmit and receive coils and a separate transmitter and receiver. It is understood that the radio frequency coil and the radio frequency transceiver are simply representative. The radio frequency antenna is intended to also represent a dedicated transmit antenna and a dedicated receive antenna. Likewise the transceiver may also represent a separate transmitter and receivers.

Also within the bore of the magnet 422 is a subject support 434 for supporting a subject 436. The subject support 434 may be positioned by a mechanical positioning system 437. Within the subject 436 there is a target zone 438. The axis of gantry rotation 440 is coaxial in this particular embodiment with the cylindrical axis of the magnet 412. The subject support 434 has been positioned such that the target zone 438 lies on the axis 440 of gantry rotation. The radiation source 408 is shown as generating a radiation beam 442 which passes through the collimator 303 and through the target zone 438. As the radiation source 408 is rotated about the axis 440 the target zone 438 will always be targeted by the radiation beam 442. The radiation beam 442 passes through the cryostat 414 of the magnet. The magnetic field gradient coil 424 has a gap 443 which separate the magnetic field gradient coil into two sections. The gap 443 reduced attenuation of the radiation beam 442 by the magnetic field gradient coil 424. In some embodiments the radio frequency coil 428 may also have gaps or be separated to reduce attenuation of the radiation beam 442.

The transceiver 430, the magnetic field gradient coil power supply 426 and the mechanical positioning system 437 are all shown as being connected to a hardware interface 446 of a computer system 444. The computer system 444 is shown as further comprising a processor 448 for executing machine executable instructions and for controlling the operation and function of the therapeutic apparatus. The hardware interface 446 enables the processor 448 to interact with and control the therapeutic apparatus 400. The processor 448 is shown as further being connected to a user interface 450, computer storage 452, and computer memory 454.

The computer storage 452 is shown as containing a radiotherapy plan 456. The radiotherapy plan 456 contains data for performing the treatment of the target zone 438. In some embodiments the radiotherapy plan 456 may contain data which allows the identification of the target zone 438 in relation to anatomical landmarks of the subject 436. The computer storage 452 is shown as further containing magnetic resonance data 458 that has been acquired by the magnetic resonance imaging system 404. There is also a magnetic resonance image 460 stored within the computer storage 452. The magnetic resonance image 460 was reconstructed from the magnetic resonance data 458. Within the computer storage 452 is a registered location 462 of the target zone 438. Also within the computer storage 452 are radiotherapy control signals 464 and mechanical positioning control signals 466.

The computer memory 452 is shown as containing computer executable instructions. The same instructions could also be stored in duplicate in the computer storage 452. The computer memory 454 is shown as containing a control module 468. The control module 468 contains computer executable instructions for operating and controlling the therapeutic apparatus 400. The computer memory 454 is shown as further containing an image reconstruction module 470. The image reconstruction module 470 was used to reconstruct the magnetic resonance image 460 from the magnetic resonance data 458. The computer memory 454 is shown as further containing an image registration module 472.

The image registration module 472 was used to generate the registered location 462 of the target zone 438 using the magnetic resonance image 460. The computer memory 454 is further shown as containing a radiation control signal generation module. The radiation control signal generation module 474 contains computer executable code for generating the radiotherapy control signals 464. The computer memory 454 is shown as further containing mechanical positioning control signal generation module 476. The mechanical positioning control signal generation module 476 contains computer executable code for generating the mechanical positioning control signals 466. The radiation control signal generation module 464 and the mechanical positioning control signal generation module 476 may use the registered location 462 and also in some embodiments the radiotherapy plan 456 for generating the radiotherapy control signals 464 and the mechanical positioning control signals 466.

Figure 5:
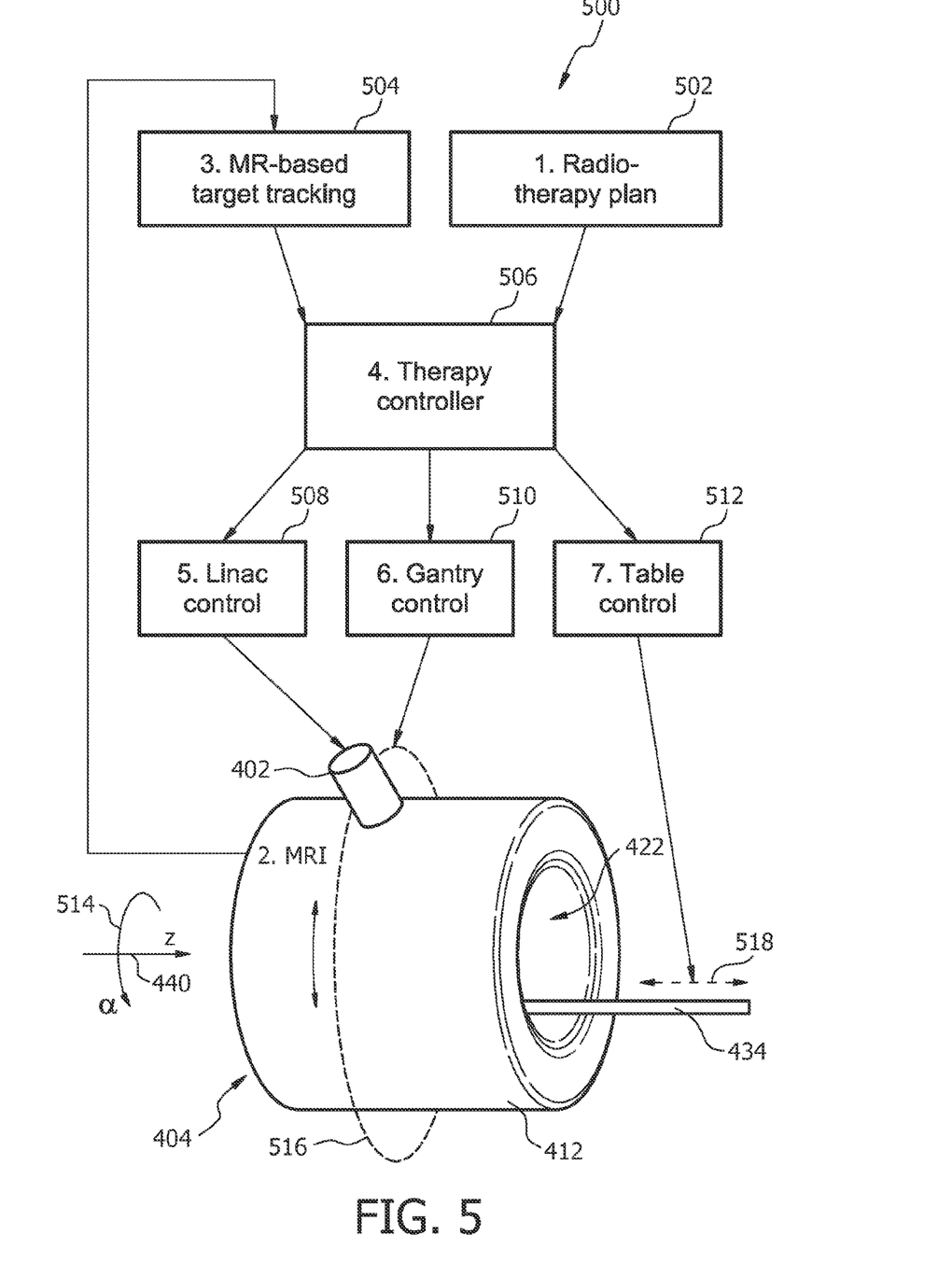
FIG. 5 shows a diagram which illustrates the functioning of a therapeutic apparatus according to an embodiment of the invention.

FIG. 5 shows a diagram which illustrates the functioning of a therapeutic apparatus 500 according to an embodiment of the invention. The block labeled 502 represents a radiotherapy plan. Magnetic resonance data is then acquired by magnetic resonance imaging system 404. The magnetic resonance data is then used to perform magnetic resonance based target tracking 504. A therapy controller or therapy control software module 506 is then used to generate and send control signals to the various components of the therapeutic apparatus 500. The magnetic resonance based target tracking 504 in combination with a therapeutic controller 506 are equivalent to the software modules stored within the computer memory 454 of FIG. 4. The therapy controller 506 then sends commands to a Linac or radiotherapy source controller 508. The therapy controller 506 also sends commands to a gantry control system 510. The therapy controller 506 also sends commands to a table controller 512. The Linac or radiation source controller 508 controls the operation of a radiotherapy source 502. The gantry controller 510 controls the rotation of the radiotherapy source 502 around a rotation path 516. The angle 514 is the angled position of the radiotherapy source 402. The table controller 512 is able to control the position of the subject support 434 by using a mechanical positioning system. The arrow 518 shows the direction of travel of the subject support 434. In this case the subject support 434 is moving identically along the z-axis or the axis of gantry rotation 440.

The flow chart in FIG. 5 shows the control-loop of the proposed MLC-free system. Usually a radiotherapy plan 502 will be available before the radiotherapy session begins (based on CT or MR). This includes an optimized trajectory of the therapy beam ("dose painting") and the patient is positioned accordingly on the patient table. A pre-scan of the patient is performed with the MR device 404 which allows to locate the target region(s) within the patient and to co-register patient-, MR/RT- and therapy plan coordinate systems 504. This information is then used by the therapy controller 506 to calculate and adjust the timing and intensity of the radiation source 508, the precise angular position α of the RT-gantry/LINAC 510 and the corresponding position of the patient (table) along the z-axis 512.

Based on the therapy plan and continuous real-time MR imaging the therapy controller can update radiation intensity and beam focus (via gantry and patient table) continuously until the prescribed dose is reached in the target region(s).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Figure 6:
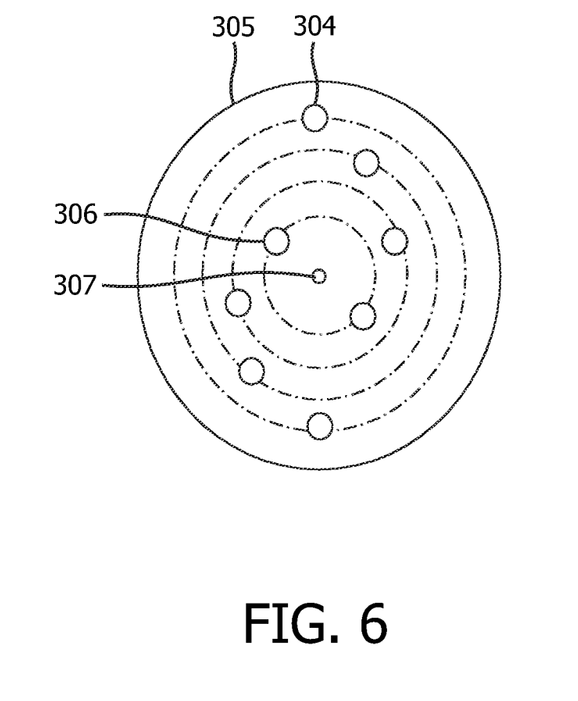
FIG. 6 shows a frontal view of the rotatable disk of one aspect of the invention.

FIG. 6 shows a frontal view of the rotatable disk of one aspect of the invention. That is, FIG. 6 shows the rotatable disk along the propagation direction of the pencil beam path when the rotatable disk is mounted in the therapeutic apparatus.

The rotatable disk 305 has several channels 304, 306 that run transverse to the surface of the disk. The body of the disk is opaque, i.e. not transparent for the radiation from the radiotherapy source. The channels are transparent for the radiation. As shown in the Figure, the various channels 304, 306 are at different radial position relative to the centre of rotation 307. The various channels are also at different azimuthal orientations relative to the centre of rotation.

Figure 7:
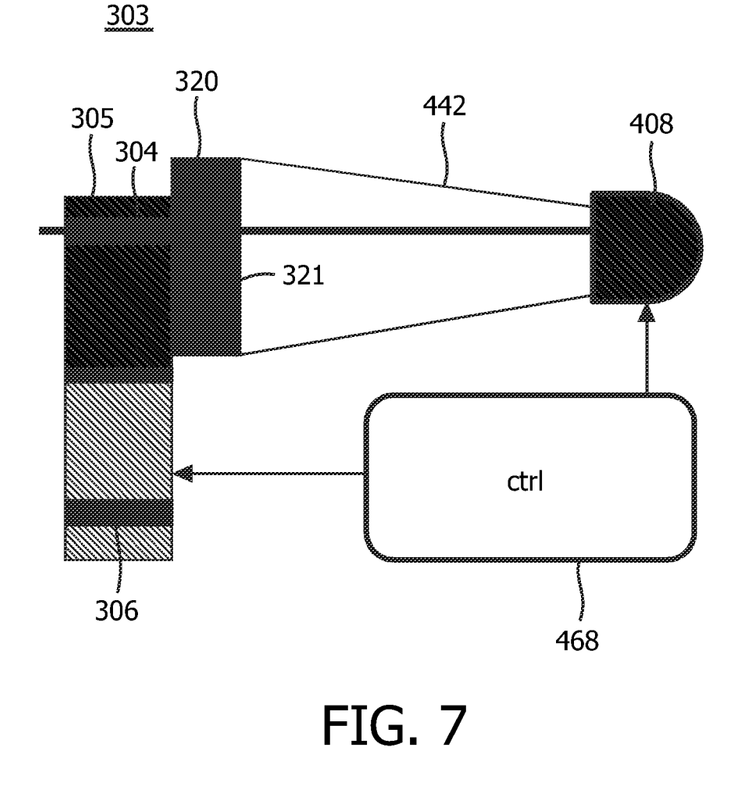
FIG. 7 shows a side elevation of the collimator assembly of one aspect of the invention.

FIG. 7 shows a side elevation of the collimator assembly of one aspect of the invention. The rotatable disk 305 is mounted next to the aperture block 320 and such that only one of the channels 304, 306 is in correspondence with the radiation transparent window 321 of the aperture block. The radiation transparent window may for example be an opening normally filled with air through which the radiation from the radiotherapy pass can propagate without substantial attenuation or absorption. The radiation transparent window may also be formed as a window of radiation transparent material. The aperture block 320 is fixedly mounted to the structure of the radiotherapy apparatus. When the rotatable disk is rotated, another of the channels can be brought into correspondence with the radiation transparent window 321. Then from the radiation beam 442 that is emitted by the radiotherapy source 408 a narrow pencil beam is formed at the exit of the channel 304 that is brought into correspondence with the window 321 of the aperture block. The spatial location of the pencil beam that exits from the rotatable disk is determined by the position of the channel at issue. Thus, when the rotatable disk is rotated and another channel is brought into correspondence with the window of the aperture block, and when the radiotherapy source is switched on when the rotatable disk is in its selected position, the pencil beam is formed at another location, viz. of that the channel at issue. Thus, by rotating the rotatable disk and switching on or off, the location of the pencil beam, and hence the location where the pencil beam impinges on the object to be irradiated is controlled. The controller 468 is configured to control the rotation of the rotatable disk and the activation of the radiotherapy source 408 on the basis of the radiotherapy plan.

Figure 8:
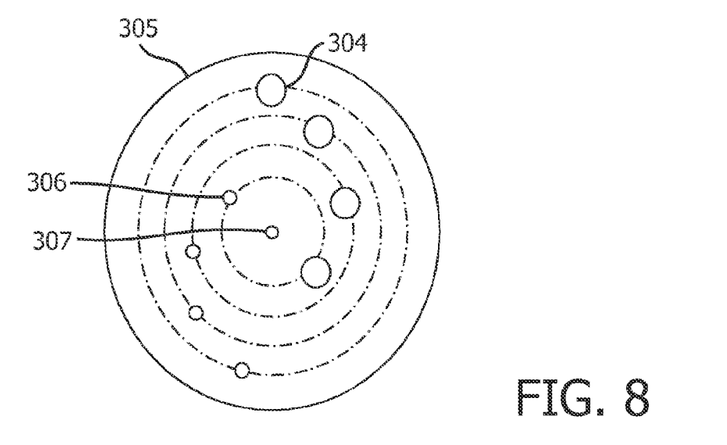
FIG. 8 shows a frontal view of the rotatable disk with groups of channels with different diameters within the rotatable disk for different pencil beam diameters.
Figure 9:
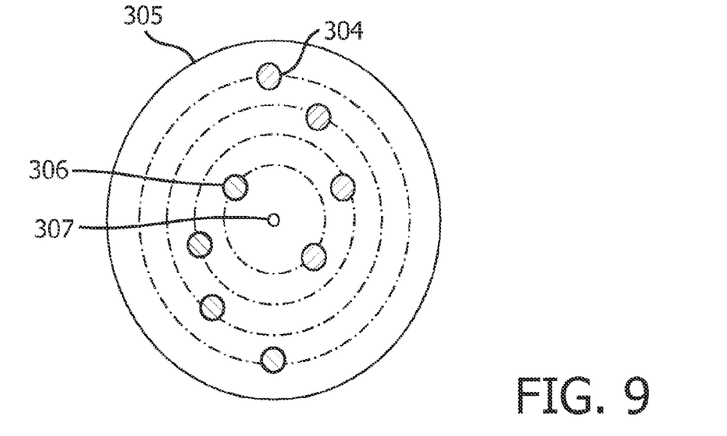
FIG. 9 shows a frontal view of the rotatable disk filling of the channels with different (weakly) radiation absorbing media for intensity modulation and FIG. 10 shows a frontal view of the rotatblwe disk a spiral notch (instead of discrete holes in the rotating disk) for a continuous radial movement of the emerging pencil beam location.
Figure 10:
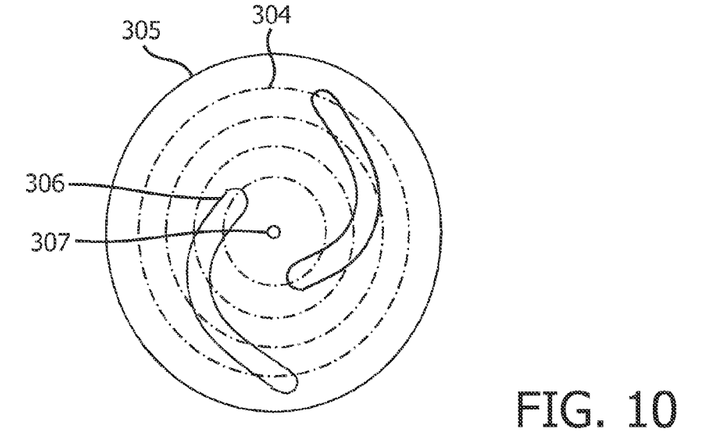

FIG. 8 shows groups of channels with different diameters within the rotatable disk for different pencil beam diameters. FIG. 9 shows filling of the channels with different (weakly) radiation absorbing media for intensity modulation. FIG. 10 shows a spiral notch 306 (instead of discrete holes in the rotating disk) for a continuous radial movement of the emerging pencil beam location.

LIST OF REFERENCE NUMERALS 200 radiation
202 target
204 primary collimator
206 beam homogonizer
208 flattenting filter
210 ion chamber
212 wedge
214 pencil collimator
300 top view
302 cross sectional view
303 cylindrical collimator assembly
304 first collimator
306 second collimator
308 third collimator
310 fourth collimator
312 bearing hole
400 therapeutic apparatus
402 radiotherapy apparatus
404 magnetic resonance imaging system
406 gantry
408 radiotherapy source
410 rotational axis
412 magnet
414 cryostat
416 superconducting coil
418 superconducting shield coil
420 low magnetic field region
422 bore
424 magnetic field gradient coil
426 magnetic field gradient coil power supply
428 radio frequency coil
430 transciever
432 imaging zone
434 subject support
436 subject
437 mechanical positioning system
438 target zone
440 axis of gantry rotation
442 radiation beam
443 gap
444 computer system
446 hardware interface
448 processor
450 user interface
452 computer storage
454 computer memory
456 radiotherapy plan
458 magnetic resonance data
460 magnetic resonance image
462 registered location of target zone
464 radiotherapy control signals
466 mechanical positioning control signals
468 control module
470 image reconstruction module
472 image registration module
474 radiation control signal generation module
476 mechanical positioning control signal generation module
500 therapeutic apparatus
502 radiotherapy plan
504 magnetic resonance imaging system
502 radiotherapy plan
504 magnetic resonance based target tracking
506 therapy controller
508 LINAC control
510 gantry control
512 table control
514 rotation angle
516 path of rotation
518 direction of table motion

The invention claimed is:

1. A therapeutic apparatus comprising:
a radiotherapy apparatus, the radiotherapy apparatus comprising:
  a radiotherapy source for directing electromagnetic radiation into a target zone;
    wherein the radiotherapy apparatus is adapted for rotating the radiotherapy source at least partially around a subject support,
    wherein the radiotherapy apparatus is adapted for tilting the radiotherapy source with respect to an axis of rotation of the radiotherapy source;
a mechanical positioning system for positioning a subject support;
a magnetic resonance imaging system for acquiring magnetic resonance data from an imaging zone, the magnetic resonance imaging system comprising:
  a magnet for generating a magnetic field within the imaging zone,
  wherein the target zone is within the imaging zone,
a cylindrical collimator assembly, comprising:
  a rotatable collimator member having a plurality of channels,
    wherein the rotatable collimator member comprises a rotatable disk in which each of the plurality of channels are provided at different radial distances relative to a center of rotation of the rotatable disk;
a computer processor for controlling the therapeutic apparatus; and
a computer memory containing machine executable instructions, the executable instructions arranged for execution by the computer processor, wherein execution of the instructions causes the processor to repeatedly:
  acquire the magnetic resonance data using the magnetic resonance imaging system;
  reconstruct a magnetic resonance image from the magnetic resonance data;
  register a location of the target zone in the magnetic resonance image;
  generate radiotherapy control signals in accordance with the location of the registered target zone,
    wherein the radiotherapy control signals cause the radiotherapy source to irradiate the target zone,
    wherein the radiotherapy control signals cause an angular rotation of the rotatable collimator member and the angular rotation at least partially controls the location of a beam path of the radiotherapy source in the target zone;
  generate mechanical positioning control signals in accordance with the registered target zone and the radiotherapy control signals, wherein the mechanical positioning control signals cause the mechanical positioning system to position the subject support; and
send the radiotherapy control signals to the radiotherapy system and send the mechanical positioning control signals to the mechanical positioning system.

2. The therapeutic apparatus of claim 1, wherein the radiotherapy source comprises a first pencil beam collimator.

3. The therapeutic apparatus of claim 2,
wherein the cylindrical collimator assembly comprises a plurality of pencil beam collimators,
wherein the plurality of pencil beam collimators include the first pencil beam collimator,
wherein the cylindrical collimator assembly has a rotational axis,
wherein rotation of the cylindrical shaped collimator assembly causes a selected beam collimator chosen from the plurality of pencil beam collimators to align with the beam path.

4. The therapeutic apparatus of claim 3, wherein the radiotherapy control signals cause the cylindrical collimator assembly to select the selected beam collimator.

5. The therapeutic apparatus of claim 3, wherein the angular rotation of the rotatable collimator member is controlled as a function of time.

6. The therapeutic apparatus of claim 1, wherein the radiotherapy control signals cause the radiotherapy system to perform one of,
adjusting a timing of the radiation source as a function of time,
adjusting an intensity of the radiation source as a function of time, and
controlling the rotating of the radiation as a function of time.

7. The therapeutic apparatus of claim 1, wherein the mechanical positioning control signals cause the mechanical positioning system to adjust the position of the subject support as a function of time.

8. The therapeutic apparatus of claim 1, wherein the location of the target zone is co-registered to the subject support, the radiotherapy apparatus, and the magnetic resonance imaging system.

9. The therapeutic apparatus of claim 1, wherein the radiotherapy source comprises an adjustable beam collimator, wherein the radiotherapy control signals control the beam collimator.

10. The therapeutic apparatus of claim 1, wherein the repeated execution of the machine executable instructions forms a closed control loop for directing the electromagnetic radiation into the target zone.

11. The therapeutic apparatus of claim 1, wherein the cylindrical collimator assembly is adapted for tilting the rotatable collimator member with respect to an axis of rotation of the radiotherapy source.

12. A tangible computer-readable medium, in which a computer program including non-transitory computer instructions for execution by a processor, the computer instructions directing control of a therapeutic apparatus,
wherein the therapeutic apparatus comprises a radiotherapy apparatus for treating a target zone of a subject,
wherein the radiotherapy apparatus comprises a radiotherapy source for directing electromagnetic radiation into the target zone,
wherein the radiotherapy apparatus is adapted for tilting the radiotherapy source with respect to an axis of rotation of the radiotherapy source,
wherein the radiotherapy apparatus further comprises a cylindrical collimator assembly, the cylindrical collimator assembly comprising a rotatable collimator member, the rotatable collimator member comprising a plurality of channels, the rotatable collimator member comprising a rotatable disk in which the channels are provided at different radial distances relative to a center of rotation of the rotatable disk,
wherein the therapeutic apparatus further comprises a mechanical positioning system for positioning a subject support,
wherein the therapeutic apparatus further comprises a magnetic resonance imaging system for acquiring magnetic resonance data from an imaging zone,
wherein the target zone is within the imaging zone,
wherein the magnetic resonance imaging system comprises a magnet for generating a magnetic field within the imaging zone,
wherein the radiotherapy apparatus is adapted for rotating the radiotherapy source at least partially around the subject support,
wherein execution of the instructions causes the processor to repeatedly:
acquire the magnetic resonance data using the magnetic resonance imaging system;
reconstruct a magnetic resonance image from the magnetic resonance data;
register a location of the target zone in the magnetic resonance image;
generate radiotherapy control signals in accordance with the location of the registered target zone,
wherein the radiotherapy control signals cause the radiotherapy source to irradiate the target zone,
wherein the radiotherapy control signals cause an angular rotation of the rotatable collimator member and the angular rotation at least partially controls the location of a beam path of the radiotherapy source in the target zone;
generate mechanical positioning control signals in accordance with the registered target zone and the radiotherapy control signals, wherein the mechanical positioning control signals cause the mechanical positioning system to position the subject; and
send the radiotherapy control signals to the radiotherapy system and send the mechanical positioning control signals to the mechanical positioning system.

13. A method of controlling a therapeutic apparatus,
wherein the therapeutic apparatus comprises a radiotherapy apparatus for treating a target zone of a subject,
wherein the radiotherapy apparatus comprises a radiotherapy source for directing electromagnetic radiation into the target zone,
wherein the radiotherapy apparatus is adapted for tilting the radiotherapy source with respect to an axis of rotation of the radiotherapy source,
wherein the radiotherapy apparatus further comprises a collimator assembly, the collimator assembly comprising a rotatable collimator member, the rotatable collimator member comprising a plurality of channels, wherein the rotatable collimator member is a rotatable disk in which the channels are provided at different radial distances relative to a center of rotation of the rotatable disk,
wherein the therapeutic apparatus further comprises a mechanical positioning system for positioning a subject support,
wherein the therapeutic apparatus further comprises a magnetic resonance imaging system for acquiring magnetic resonance imaging data from an imaging zone,
wherein the target zone is within the imaging zone,
wherein the magnetic resonance imaging system comprises a magnet for generating a magnetic field within the imaging zone, wherein the radiotherapy apparatus is adapted for rotating the radiotherapy source at least partially around the subject support wherein the method comprises repeatedly performing the steps of:

acquiring the magnetic resonance data using the magnetic resonance imaging system;

reconstructing a magnetic resonance image from the magnetic resonance data;

registering a location of the target zone in the magnetic resonance image;

generating radiotherapy control signals in accordance with the location of the registered target zone,
  wherein the radiotherapy control signals cause the radiotherapy source to irradiate the target zone,
  wherein the radiotherapy control signals cause an angular rotation of the rotatable collimator member and the angular rotation at least partially controls the location of a beam path of the radiotherapy source in the target zone;

generating mechanical positioning control signals in accordance with the registered target zone and the radiotherapy control signals, wherein the mechanical positioning control signals cause the mechanical positioning to position the subject;

sending the radiotherapy control signals to the radiotherapy system; and sending the mechanical positioning control signals to the mechanical positioning system.

* * * * *